July 14, 1953 H. M. TIRET Plant Pat. 1,204
FUCHSIA PLANT
Filed Feb. 27, 1952
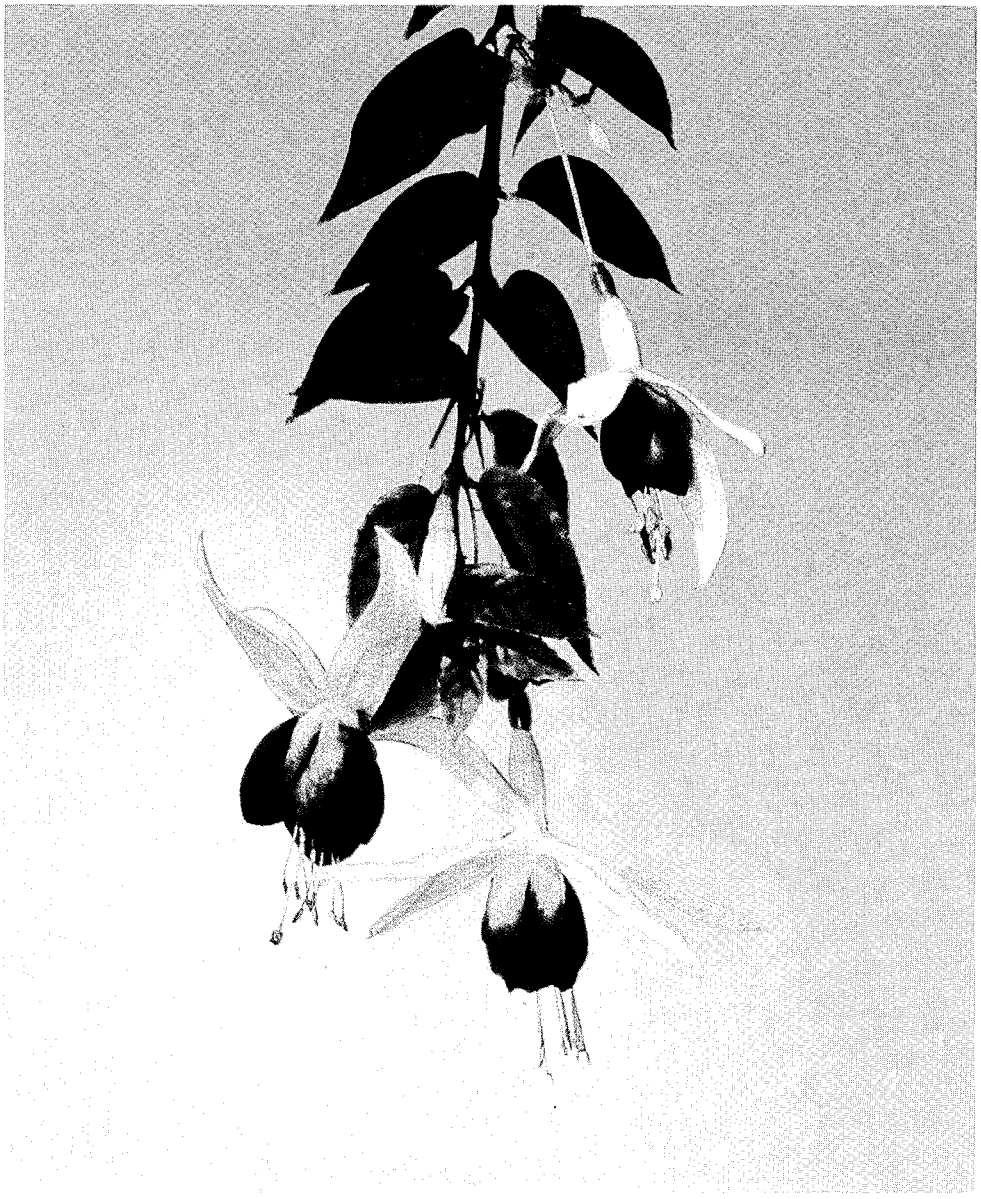
Inventor
Horace M. Tiret Patented July 14, 1953

Plant Pat. 1,204

UNITED STATES PATENT OFFICE 1,204

FUCHSIA PLANT

Horace M. Tiret, San Francisco, Calif.

Application February 27, 1952, Serial No. 273,707

1 Claim. (Cl. 47—60)

This invention relates to a new and improved fuchsia plant, the principal new and different characteristics of which is the deep, purple color of the petals contrasted with the extremely long, white, flesh pink sepals.

The plant was derived as a hybrid from seedlings (unpatented) not introduced to the trade, namely 1/6/1 by 3/36/5, the figures representing applicant's own breeding symbols. The fuchsia plant is distinguished principally by its pale green foliage, vigorous habit of growth, and distinctive deep, purple coloring, which has not previously been found in this combination in any fuchsia plant, and has been asexually reproduced at Palo Alto, Santa Clara County, California, by cuttings which retained the characteristics of the parent fuchsia.

The plant is a trailing variety, but may also be trained as an upright, and grows vigorously, throwing numerous branches during the process of growth. When the plant blooms, the long, white buds with green tips open into medium-large, semi-double flowers. The bud is white, and the flower is a deep, doge purple (#732 Horticultural Color Chart). The base of the outer petals is pale phlox pink (#625/3 Horticultural Color Chart). The flower has no fragrance.

In the accompanying drawing, the figure shows a typical branch tip including both a bud and fully opened blossom, the drawing representing approximately actual size.

A detailed description of this new variety of fuchsia plant follows:

*Habit of growth.*—Strong trailing variety which throws out branches from the roots and whose branches in turn are self-branching to form a full basket. Flowers occur both along the stem and at the tips of the branches.

*Foliage.*—Medium sized, light green leaves heavily veined, having serrated edges and evenly spaced along the branch. The leaves are of a general, slender heart shape, and taper to pointed tips. Buds are long ovoid in shape, being well pointed, and have a color of white with faint green shading.

*Flower.*—The flower is semi-double, of medium large size for the genus. The corolla is tightly pressed through overlapping of the petals, forming a closed and solid group. The flower is strongly resistant to wilting at high atmospheric temperature, but grows equally well in the cooler, coastal climate of the west. The color is a deep doge purple (#733 Horticultural Color Chart), which is the outstanding, distinctive and different feature of this plant, with pale phlox pink (#625/3 Horticultural Color Chart) at the base of the petals, and veining the inner petals.

*Ovary.*—Small and light green.

*Tube.*—Medium size, slender tube having the same color as the bud.

*Petals.*—From eight to twelve petals occur to each flower, and the petals overlap forming a tight bunch. As the flower matures, the petals retain their overlapped and tightly bunched form. The petals are deep doge purple, with incidental phlox pink coloring at the base, all as above described.

*Stamens.*—The stamens are long, approximately 1¾ inches in length, measured from the seed pod, and of a maroon color, and terminate short of the long pistil, approximately 2¾ inches in length, measured from the seed pod, having a yellow tip which hangs below the cluster of stamens.

*Sepals.*—The sepals are extremely long, medium thin, and gondola shaped, colored on the underside pale phlox pink with green tips, and on the top off-white with faint phlox pink veining. The texture is crepe-like on the underside and smooth on the top.

*Parentage.*—Applicant's own seedlings (unpatented) and not introduced to the trade, applicant's breeding symbols 1/6/1 and 3/36/5.

It is noted that the foliage and flowers will vary somewhat with the seasons and growing conditions; however, the fuchsia plant is clearly differentiated from others by the deepness and exceptional character of its deep doge purple coloring.

Having thus disclosed my discovery I claim:

The new and distinct variety of fuchsia plant herein described and illustrated, characterized by the distinctive deep doge purple color of the petals, combined with the extremely long, white, flesh pink sepals.

HORACE M. TIRET.

References Cited in the file of this patent

UNITED STATES PATENTS

| Number | Name | Date |
|---|---|---|
| Pl. Pt. 1,110 | Waltz | July 1, 1952 |